US005637083A

United States Patent [19]

Bertrand et al.

[11] Patent Number: 5,637,083

[45] Date of Patent: Jun. 10, 1997

[54] IMPLANTABLE ADJUSTABLE FLUID FLOW CONTROL VALVE

[75] Inventors: William J. Bertrand, Ventura, Calif.; David A. Watson, East Greenwich, R.I.

[73] Assignee: Pudenz-Schulte Medical Research Corporation, Goleta, Calif.

[21] Appl. No.: 588,822

[22] Filed: Jan. 19, 1996

[51] Int. Cl.$^6$ .................... A61M 5/00

[52] U.S. Cl. .................... 604/9; 604/248

[58] Field of Search .................... 604/8–10, 247, 604/248

[56] References Cited

U.S. PATENT DOCUMENTS

| | | |
|---|---|---|
| 3,391,289 | 7/1968 | Danilewicz et al. . |
| 4,156,422 | 5/1979 | Hildebrandt et al. . |
| 4,340,038 | 7/1982 | McKean . |
| 4,360,007 | 11/1982 | Levy et al. . |
| 4,387,715 | 6/1983 | Hakim et al. . |
| 4,443,214 | 4/1984 | Marion . |
| 4,552,553 | 11/1985 | Schulte et al. . |
| 4,560,375 | 12/1985 | Schulte et al. . |
| 4,595,390 | 6/1986 | Hakim et al. . |
| 4,636,194 | 1/1987 | Schulte et al. . |
| 4,741,730 | 5/1988 | Dormandy, Jr. et al. . |
| 4,761,158 | 8/1988 | Schulte et al. . |
| 4,781,673 | 11/1988 | Watanabe . |
| 4,781,674 | 11/1988 | Redmond et al. . |
| 4,795,437 | 1/1989 | Schulte et al. . |
| 4,850,955 | 7/1989 | Newkirk . |
| 4,861,331 | 8/1989 | East et al. . |
| 4,867,740 | 9/1989 | East . |
| 4,867,741 | 9/1989 | Portnoy . |
| 4,995,864 | 2/1991 | Bartholomew et al. . |
| 5,154,693 | 10/1992 | East et al. . |
| 5,167,615 | 12/1992 | East et al. . |
| 5,176,627 | 1/1993 | Watson . |

*Primary Examiner*—John G. Weiss
*Assistant Examiner*—Ki Yong O
*Attorney, Agent, or Firm*—Kelly, Bauersfeld, Lowry & Kelley

[57] ABSTRACT

A subcutaneously implantable and percutaneously adjustable fluid flow control device includes a magnetically adjustable valve for controlling fluid flow from an inlet to an outlet. The valve includes a housing having a fluid passageway therethrough, a valve element designed to bear upon a valve seat to close the passageway to fluid flow, and a spring which biases the valve element against the valve seat so as to keep the passageway closed until a fluid pressure differential between the inlet and the outlet exceeds a selected valve opening pressure. A fixed dual concentric stair-step array and an overlying rotor assembly permit the amount of bias applied to the valve element by the spring to be adjusted. The rotor assembly is adapted to rotate in response to an external or percutaneously-applied magnetic field. In one embodiment, the rotor assembly may be locked into one of several possible rotational positions relative to the stair-step array to prevent rotation thereof.

30 Claims, 4 Drawing Sheets

FIG-5
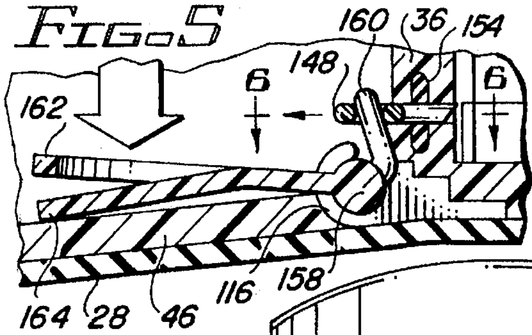
FIG-6
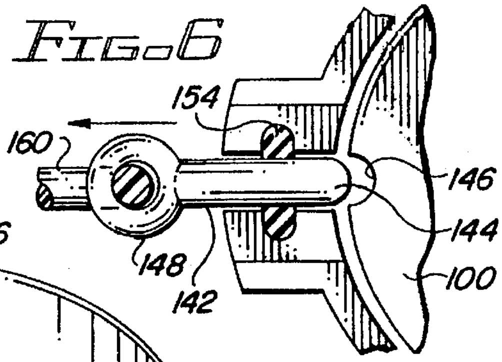
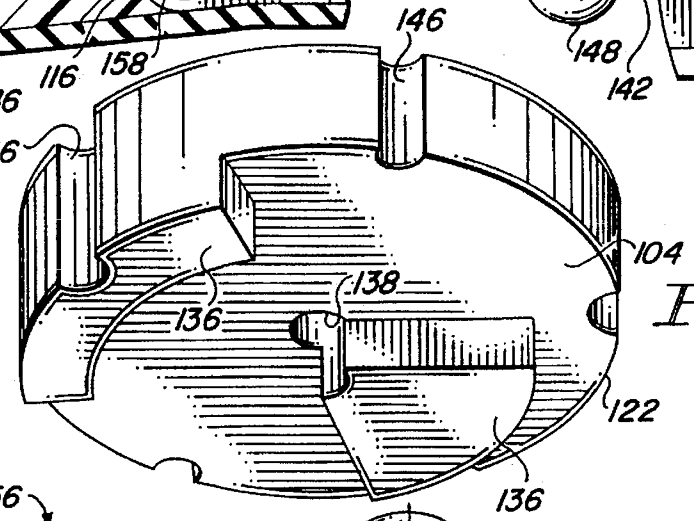
FIG-9
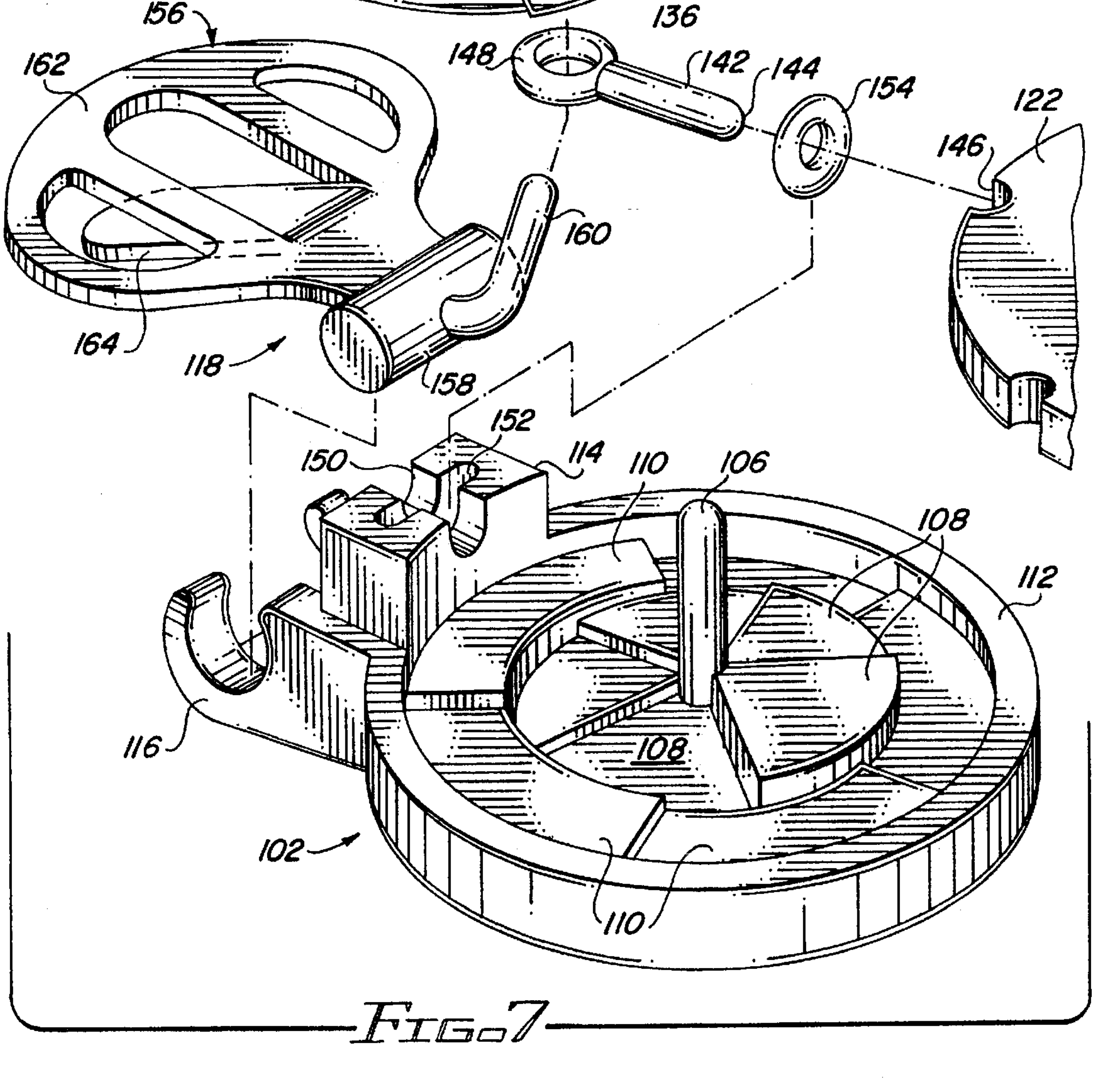
FIG-7

FIG. 8
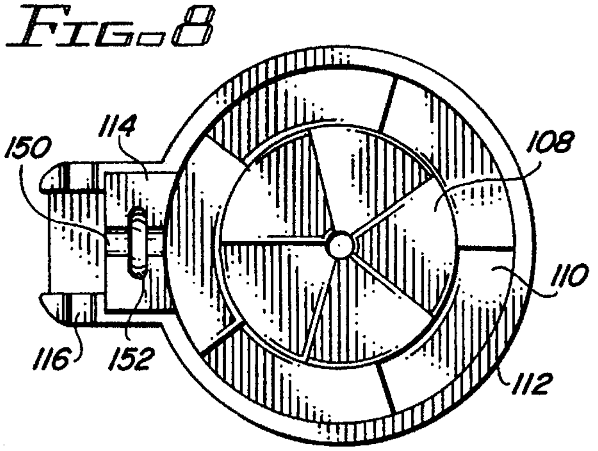
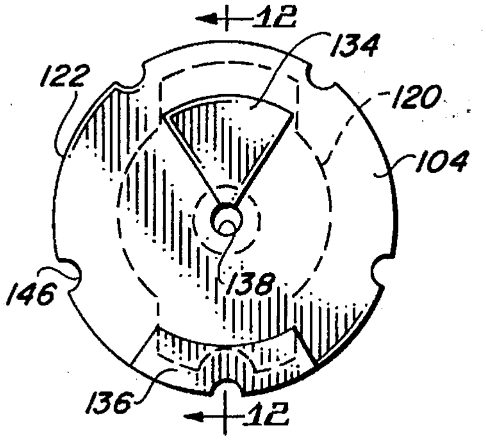
FIG. 10
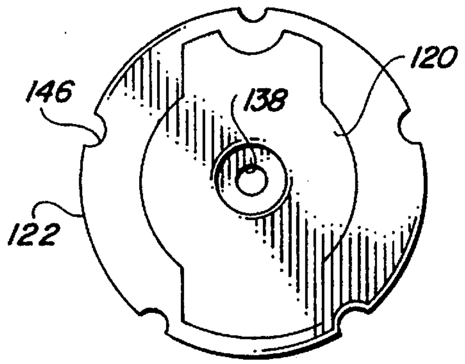
FIG. 11
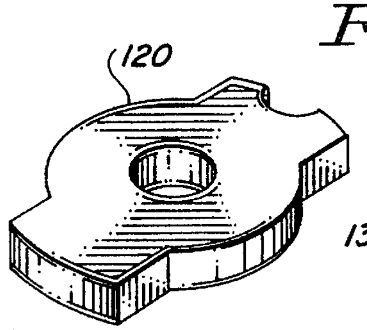
FIG. 13
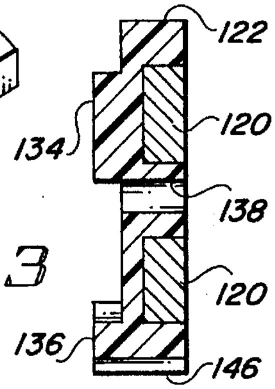
FIG. 12
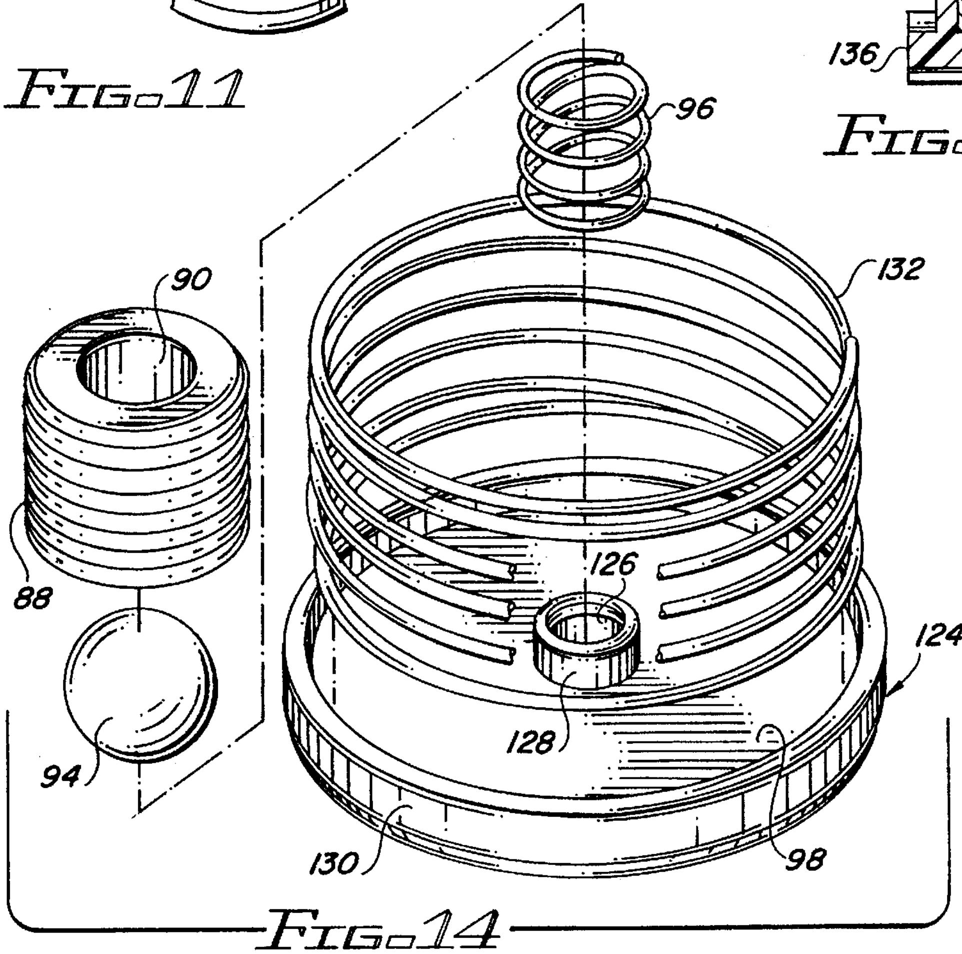
FIG. 14

IMPLANTABLE ADJUSTABLE FLUID FLOW CONTROL VALVE

BACKGROUND OF THE INVENTION

This invention relates generally to surgically implanted physiological shunt systems and related flow control devices. More particularly, the present invention relates to shunt systems including one-way flow control valves for controlling the flow of cerebrospinal fluid out of a brain ventricle and preventing backflow of fluid into the brain ventricle.

In the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids accumulate within the skull and exert extreme pressure and skull deforming forces.

In treating hydrocephalus, cerebrospinal fluid accumulated in the brain ventricles is typically drained away utilizing a drainage or shunt system including a catheter inserted into the ventricle through the skull, which is connected to a tube that conducts the fluid away from the brain to be reintroduced into the peritoneal cavity or into the vascular system, as by extending a distal catheter through the patient's jugular vein to the atrium portion of the heart. To control the flow of cerebrospinal fluid and maintain the proper pressure in the brain ventricle, a pump or valve is placed in the conduit between the brain and the peritoneal cavity or the heart. An exemplary flow control device is found in U.S. Pat. No. 4,560,375.

Although such drainage systems have provided successful results, a problem of overdrainage of the cerebrospinal fluid from the brain ventricles sometimes exists. Overdrainage of cerebrospinal fluid may result in excessive reduction of the cerebrospinal fluid pressure within the brain ventricles and predispose the development of a subdural hematoma or hydroma, and excessive reduction of ventricular size leading to shunt obstruction because of impingement of the ventricular walls on the inlet holes of the ventricular catheter. This overdrainage can be caused by the siphoning effect of hydrostatic pressure in the distal shunt catheter. The siphoning effect of hydrostatic pressure may be created by the elevation of the ventricular catheter inlet with respect to the distal catheter outlet (i.e., when the patient sits, stands or is held erect). In order to prevent such overdrainage caused by the siphoning effect of hydrostatic pressure in the distal shunt catheter, siphon control devices have been placed in the conduit, typically between the flow control device and the peritoneal cavity or the heart. An exemplary siphon control device is found in U.S. Pat. No. 4,795,437.

It is desirable in some instances to permit the physician to be able to alter the flow characteristics through the drainage system after it has been subcutaneously implanted. To this end, on-off devices have been provided for implantation as a portion of the fluid conduit as an additional element of the shunt. An exemplary on-off device is shown in U.S. Pat. No. 3,827,439. Moreover, flow control devices have been provided which utilize a plurality of flow control valves having different flow control characteristics, which provide, alternative fluid pathways therethrough such that selection of a desired fluid pathway can be made by the selective percutaneous manipulation of the device when subcutaneously implanted. Such flow control devices having selectable alternative fluid pathways are shown in U.S. Pat. Nos. 5,154,693 and 5,167,615, the contents of which are incorporated herein.

These prior fluid shunt devices have all shared one important limitation: they only permit fluid flow therethrough upon achieving at most two fluid pressure differentials at the inlet and outlet of the device. In treating hydrocephalus, however, it is often desirable to vary the device "opening" pressure differential in accordance with ventricle size and treatment objective. For example, initial treatment may require a lower than normal pressure differential to initiate shrinkage of the ventricles, but as the ventricles decrease in size, the pressure differential should be increased gradually so that when the ventricle is returned to normal size the intraventricular pressure is at its normal value and the intracranial force systems are in balance (i.e., the opening differential pressure is set at a level that will stabilize the ventricles at a desired size). Generally speaking, the opening differential pressure should be varied inversely with the ventricle size. It is desirable to leave a lower pressure valve in a patient after the ventricles are again normal size, because the ventricles can further collapse, leading to a condition known as "slit" ventricles.

A further reason for providing adjustability in the opening pressure differential is to correct for variations in nominal opening pressure differentials typical in manufactured valves. With an adjustable valve, the opening pressure differential can be more accurately set at the factory and can be checked and corrected if necessary in the operating room prior to implantation.

Accordingly, there has been a continuing need in the medical arts for convenient and effective physiological drainage systems for controlling the flow of fluid from one part of the body to another, which are relatively inexpensive to manufacture, permit fluid flow therethrough only when upstream fluid pressure exceeds downstream fluid pressure by a selected pressure differential, and also provide means for altering the selected pressure differential by percutaneous manipulation of the device when it is subcutaneously implanted. Moreover, such a flow control device is needed which incorporates an integral siphon control device that opens only in response to positive upstream fluid pressure, and recloses or remains closed in the absence of such positive upstream fluid pressure or in response to negative downstream hydrostatic pressure on the device. As will become apparent from the following description, the present invention satisfies these needs and provides other related advantages.

SUMMARY OF THE INVENTION

The present invention resides in an improved subcutaneously implantable and percutaneously adjustable fluid flow control device useful in a physiological shunt system for controlling the flow of fluid from one part of the body to another. The fluid flow control device of the present invention includes components responsive to an external or percutaneously-applied magnetic field, to provide the device a variety of pressure/flow characteristics. In accordance with the present invention, the fluid flow control device comprises an inlet, an outlet and valve means for controlling the fluid flow from the inlet to the outlet. The valve means comprises a valve housing including a fluid passageway therethrough which has a peripheral surface that forms a valve seat, and a valve element having a diameter larger than the valve seat. Means are provided for biasing the valve element against the valve seat so as to keep the fluid passageway closed until a fluid pressure differential between the inlet and the outlet exceeds a selected valve opening pressure. Further, a pump is situated between the inlet and the valve means. The pump provides means for flushing fluid through the device by the application of percutaneous pressure to the pump.

In one preferred form of the invention, the valve housing includes a threaded aperture and a flow regulator insert which is threaded into the aperture to define the fluid passageway. Means are provided for adjusting the amount of bias applied to the valve element by the biasing means. In particular, the adjusting means includes a fixed dual concentric stair-step array and an overlying rotor assembly having a first surface which supports an end of a valve element-biasing spring, and a second surface which is supported by the stair-step array. The rotor assembly is adapted to rotate in response to an external or percutaneously-applied magnetic field and such rotation of the rotor assembly permits selected seating of the second surface on the stair-step array to raise or lower the rotor assembly with respect to the stair-step array.

The dual concentric stair-step array includes a central rotor pivot, a plurality of inner steps surrounding the rotor pivot, and a plurality of outer steps extending peripherally about the inner steps. The rotor assembly includes a magnet embedded within a base having an inner leg adapted to bear against a selected one of the plurality of inner steps, and outer leg disposed diametrically opposite the inner leg and adapted to bear against a selected one of the plurality of outer steps, a central aperture through which the rotor pivot extends, and a rotor cap fixed to the base on a side thereof opposite the inner and outer legs. The rotor cap provides the first surface of the rotor assembly and includes a central aperture aligned with the central aperture of the base, through which the rotor pivot extends.

A compression spring is provided between a portion of the valve housing surrounding the fluid passageway and the first surface of the rotor assembly. The compression spring biases the rotor assembly into contract with the dual concentric stair-step array.

Means are also provided for occluding a portion of the fluid flow control device adjacent to the inlet by application of manual percutaneous pressure to the device. Similarly, means are provided for occluding a portion of the fluid flow control device adjacent to the outlet also by application of manual percutaneous pressure to the device. Moreover, a siphon control device is situated between the valve and the outlet.

In another preferred form of the invention, means are provided for locking the rotor assembly into one of several possible rotational positions relative to the stair-step array to prevent rotation thereof. Further, means are provided for disengaging the locking means to permit rotation of the rotor assembly in response to the external magnetic field. More particularly, the locking means comprises a pin having a first end that engages one of a plurality of detents in an outer peripheral surface of the rotor assembly to prevent rotation thereof. The disengaging means comprises pin actuating means for moving the pin between a first extended position, wherein the end of the pin engages one of the plurality of detents, and a second retracted position. The pin actuating means comprises a pivotable lever including a pin engaging shaft that engages a second end of the pin, and a manually actuated lever disposed within the pump and biased so as to urge the pin into its first position.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 5 is a fragmented vertical section similar to FIG. 3, illustrating the manner in which a lever disposed within a pump reservoir of the device is depressed to disengage a lock;

FIG. 6 is an enlarged, fragmented and partially sectional view taken generally along the line 6—6 of FIG. 5;

FIG. 7 is an exploded perspective view of components of a valve assembly of the fluid flow control device, including a fixed dual concentric stair-step array, a portion of an overlying rotor assembly, a pin reciprocable through an O-ring positioned within a supporting bracket of the stair-step array, and an actuating mechanism pivotable with respect to a lock lever pivot holder attached to the stair-step array, which provides means for reciprocating the pin into and out of detents provided in the outer peripheral surface of the rotor assembly;

FIG. 8 is a top plan view of the fixed dual concentric stair-step array of FIG. 7;

FIG. 9 is a bottom and side perspective view of the rotor assembly base partially shown in FIG. 7;

FIG. 10 is a bottom plan view of the rotor assembly base of FIG. 9;

FIG. 11 is a top plan view of the rotor assembly base of FIGS. 9 and 10;

FIG. 12 is a sectional view of the rotor assembly base taken generally along the line 12—12 of FIG. 10;

FIG. 13 us a top and side perspective view of a magnet embedded within the rotor assembly base of FIGS. 9–12;

FIG. 14 is an exploded perspective view illustrating additional components comprising the valve, in addition to those illustrated in FIG. 7, namely a rotor cap positionable over a top surface of the rotor assembly base, a pressure spring which extends between an upper surface of the rotor cap and a ruby ball valve element, a return compression spring which extends between an upper surface of the rotor cap and a portion of a valve housing, and a threaded flow regulator housing which defines a fluid passageway therethrough;

DETAILED DESCRIPTION OF THE PREFERRED EMBODIMENTS

Figure 3:
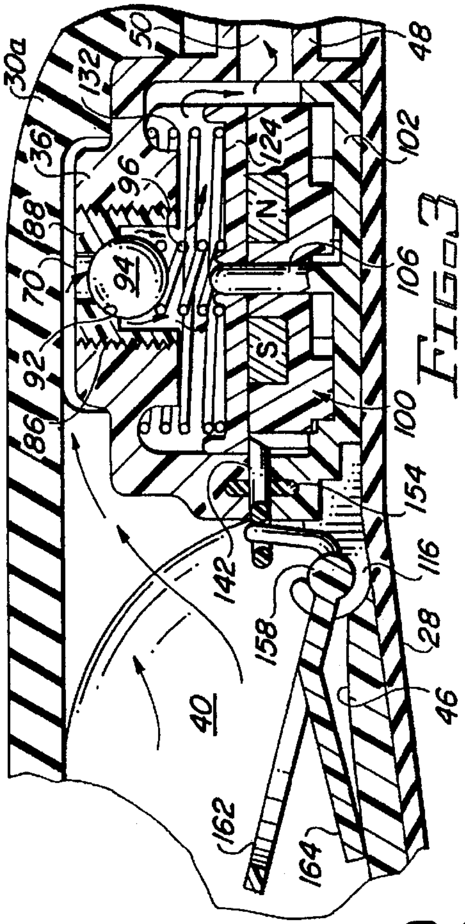
FIG. 3 is an enlarged fragmented sectional view taken of the area designed by the line 3 in FIG. 2.

As shown in the drawings for purposes of illustration, the present invention is concerned with a subcutaneously implantable and percutaneously adjustable fluid flow control device, generally designated in the accompanying drawings by the reference numbers 20 (FIGS. 1–14) and 20' (FIGS. 15–18). The improved fluid flow control devices 20 and 20' are intended for use in a surgically implanted physiological shunt system for draining fluid from one portion of the body to another. In order to connect, for example, the devices 20 or 20' in such a system, the devices include an inlet connector 22 and an outlet connector 24 which each receive one end of a piece of surgical tubing (not shown). The ends of the surgical tubing are placed over the connectors 22 and 24 and secured thereon by a single ligature just inside of an annular ridge 26 formed near the end of each connector.

When the flow control devices 20 and 20' are used in a drainage system intended for the treatment of hydrocephalus, the inlet connector 22 is fluidly connected with a proximal catheter which is inserted through the skull into a brain ventricle containing cerebrospinal fluid under pressure. The outlet connector 24 is fluidly connected to a distal catheter which serves to discharge cerebrospinal fluid to, for example, the atrium portion of a patient's heart. Ordinarily the flow control devices 20 and 20' will be surgically implanted on the patient's skull with a flap of skin overlying the device. To facilitate holding the device in its desired position after implantation, a generally flexible mounting plate 28 can be provided with one or more suture holes.

As will become apparent from the following description, the present invention provides a highly reliable fluid flow control device which has a single flow path therethrough and a valve mechanism which can be percutaneously adjusted when the device is subcutaneously implanted. The present invention is designed to facilitate implantation by eliminating components to be connected or adjusted other than the surgical tubing to the device itself.

In accordance with the present invention, the flow control devices 20 and 20' include a relatively rigid, molded plastic base invested within an elastomeric casing 30 which, together, define a fluid flow path through the fluid flow control devices from the inlet connector 22 to the outlet connector 24. The base comprises an inlet section 32 integrally formed with the inlet connector 22, an outlet section 34 integrally formed with the outlet connector 24, and an intermediate valve housing 36 disposed within the elastomeric casing 30 between the inlet and outlet sections 32 and 34. The valve housing 36 includes a percutaneously adjustable valve mechanism which restricts the flow of fluid through the device 20 or 20'. The casing 30 and the outlet segment 34 of the base cooperate to provide a siphon control device 38 situated between the valve housing 36 and the outlet connector 24, which prevents fluid flow through the devices 20 and 20' in the absence of positive upstream fluid pressure or in response to negative downstream hydrostatic pressure on the device. Further, the casing 30 and the inlet segment 32 of the base cooperate to define a pump or flushing reservoir 40 between the inlet connector 22 and the valve housing 36.

More specifically, and as shown best in FIGS. 1–3, 15 and 16, the inlet segment 32 of the base abuts against a proximal side of the valve housing 36 which, in turn, itself interfits with the outlet segment 34 of the base. The inlet segment 32 defines an inlet flow channel 42 extending through the inlet connector 22 to an upwardly facing inlet occluder port 44. The inlet segment 32 of the base forms a bottom plate 46 for the flushing reservoir 40 and an abutment support for a portion of the valve housing 36.

The valve housing 36 includes a snap-fit interlocking barbed connector 48. The barbed connector 48 extends from the valve housing 36 toward the outlet segment 34 of the base, and forms a valve outlet fluid passageway 50 for directing fluids into the siphon control device 38. A pair of splines (not shown) extend from the valve housing 36 adjacent to the connector 48 and, together with the connector 48, interact with corresponding portions of the outlet segment 34 of the base to prevent tensile and torsional movement of the valve housing 36 and the outlet segment 34 of the base with respect to one another.

The outlet segment 34 of the base is integrally formed with the outlet connector 24 which defines an outlet flow channel 52 therethrough. The outlet segment 34 defines a portion of the siphon control device 38. A connector receptacle 54 is provided in the proximal end of the outlet segment 34 for receiving the barbed connector 48 therein. Spline receiving slots (not shown) are provided in the proximal end of the outlet segment 34 to slidably receive and substantially envelope the splines as the connector 48 is inserted into the receptacle 54. A similar base connection arrangement is illustrated in detail in U.S. Pat. No. 5,176,627, the contents of which are incorporated herein.

The elastomeric casing 30 is provided in two parts: a first or inlet casing body **38*a* into which the inlet segment 32 of the base and the valve housing 36 are invested, and an outlet or second casing 30*b* which is sealed by a suitable adhesive 56 to the inlet casing 30*a* in order to provide a continuous elastomeric exterior to the devices 20 and 20', with the exception of the inlet and outlet connectors 22 and 24 which extend therefrom. The inlet casing body 30*a* is integrally formed with the mounting pad 28 and includes an inlet aperture through which the inlet connector 22 extends, an inlet occluder wing 58 which generally overlies the inlet occluder port 44, and a resiliently flexible dome 60 for the flushing reservoir 40**.

In order to provide a fluid-tight seal between the inlet connector 22 and the inlet casing body **30*a*, a tube 62 is placed over a portion of the inlet connector and secured in place by means of a Mersilene over-suture 64. A silicone adhesive 66 is then injected into any remaining gap between the casing 30 and the inlet connector 22, and is also disposed peripherally about the inlet connector 22 and adjacent the proximal end of the elastomeric casing 30. This same sealing arrangement is utilized between the outlet casing body 30*b* and the outlet connector 24**.

The inlet occluder wing 58 is positioned over the inlet occluder port 44 to facilitate occluding a portion of the fluid flow path through the devices 20 and 20' by pressing the wing 58 downwardly. Depressing the wing 58 and occluding the port 44 prevents proximal fluid flow from the flushing reservoir 40, defined by the dome 60 and the bottom plate 46, when the dome is pressed downwardly by manual percutaneous pressure. The dome 60 is preferably molded of a silicone elastomer material and is designed to permit injection into the fluid flow control devices 20 and 20' by a hypodermic needle through the dome. The inlet segment 32 of the base, as well as the outlet segment 34 and the valve housing 36, is preferably molded of a polypropylene material which provides sufficient rigidity to prevent a needle from inadvertently passing through the devices 20 and 20' if an injection is made into the flushing reservoir 40. The construction of the base segments 32, 34 and 36, and the elastomeric casing 30, helps to guide a physician in manually percutaneously manipulating the devices 20 and 20' when subcutaneously implanted, for purposes of flushing the shunt system and adjusting the valve mechanism, when needed.

A distal occluder wing 68 is positioned over the valve housing 36 to facilitate occluding a valve inlet fluid passageway 70. This is accomplished by pressing the wing 68 downwardly, which effectively prevents distal fluid flow from the flushing reservoir 40 when the dome is pressed downwardly by manual percutaneous pressure.

The outlet casing body **30*b* surrounds a portion of the outlet segment 34 of the base to define the siphon control device 38 which is similar to that shown and described in U.S. Pat. No. 4,795,437, the contents of which are incorporated herein. The siphon control device 38 includes an outer wall 72 and an inner wall 74 which is situated within and encircled about by the outer wall. The valve outlet fluid passageway 50 through the barbed connector 48 directs fluid from the valve housing 36 to a central SCD reservoir 76 defined as the area between the inner wall 74 and the outer wall 72. The outlet flow channel 52 extends through the inner wall 74 to the distal end of the outlet connector 24**.

The outer wall 72 is generally circular in shape, and is spaced from and encircles the inner wall 74. The inner wall 74 is also generally circular in shape, and defines an SCD outlet chamber 78 which is adjacent to and in fluid communication with the outlet flow channel 52. The inner wall 74 is constructed to have substantially parallel upper and lower seating surfaces 80, and it effectively forms a barrier separating the SCD reservoir 76 from the SCD outlet chamber 78.

The outlet casing body **30*b* is provided with a pair of spaced, substantially parallel, flexible elastomeric diaphragms 82 which are fixed about their peripheries adjacent to the outer wall 72. Each diaphragm 82 has an inner surface which defines the upper and lower limits of the SCD reservoir 76 and the SCD outlet chamber 78, and an outer surface which forms an exterior surface of the siphon control device 38. The diaphragms 82 are situated on opposite sides of the inner wall 74 to position a portion of each inner surface thereof in contact with an adjacent one of the seating surfaces 80 to form a seal therebetween which prevents fluid flow between the valve outlet fluid passageway 50 and the outlet flow channel 52**.

The second casing body **30*b* further includes integral offset rings 84 which surround each diaphragm 82 to inhibit overlying tissue from occluding the siphon control device 38 when implanted into a patient. An aperture is provided through the casing body 30*b* though which the outlet connector 24 extends. A fluid tight seal is effected between the casing outlet aperture and the outlet connector 24 utilizing a tube 62, an over-suture 64 and an adhesive 66 as described above in connection with the inlet casing body 30*a* and the inlet connector 22**.

In use, the diaphragms 82 normally lie against and interact with the seating surfaces 80 of the inner wall 74 to close the devices 20 and 20' to fluid flow. The diaphragms 82 move away from the seating surfaces 80, however, in response to a minimal level of positive fluid pressure within the SCD reservoir 76 to permit passage of fluid from the valve outlet fluid passageway 50 to the outlet flow channel 52. The diaphragms 82 close and seal upon the seating surfaces 80 once again in the absence of such positive upstream fluid pressure, or in response to negative downstream hydrostatic pressure in the SCD outlet chamber 78. The siphon control device 38 thus minimizes the undesirable consequences attendant to excessive overdrainage of fluid due to the siphoning effect of hydrostatic pressure.

With reference now to FIGS. 1–14, the valve mechanism of the first illustrated embodiment of the fluid flow control device 20 will be described in detail.

Figure 2:
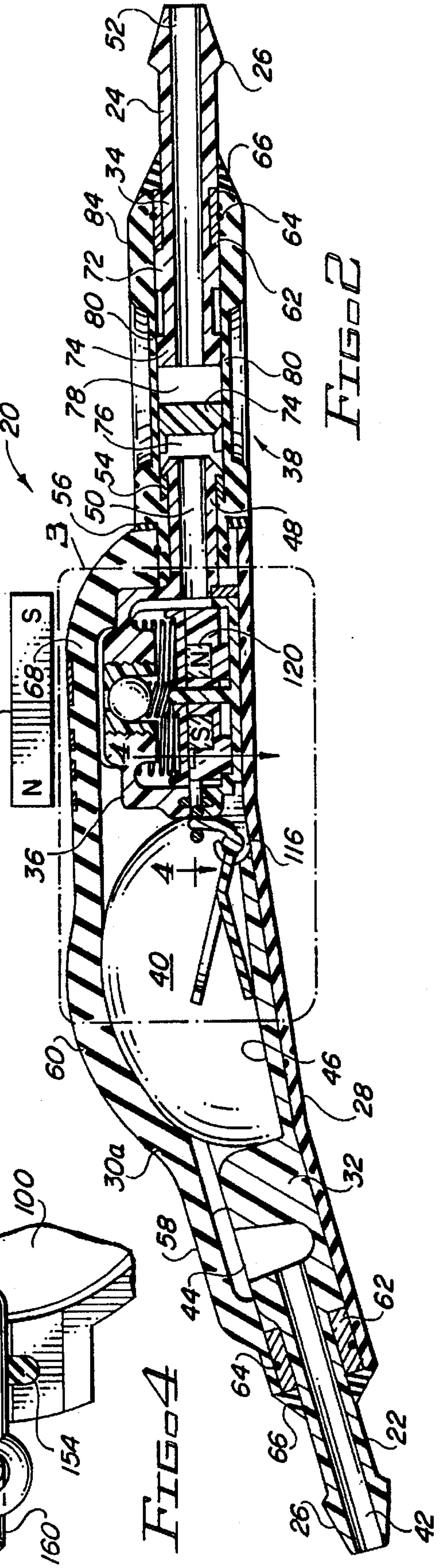
FIG. 2 is an enlarged elevational section taken generally along the line 2—2 of FIG. 1.

As illustrated best, initially, in FIGS. 2 and 3, the valve mechanism within the valve housing 36 provides means for controlling fluid flow from the inlet connector 22 to the outlet connector 24 and, more particularly, from the flushing reservoir 40 to the valve outlet fluid passageway 50. The valve housing 36 includes a central threaded aperture 86 through an upper section thereof into which is threaded a flow regulator insert 88 (See FIG. 14) which defines a fluid passageway 90 therethrough. The lower end of the flow regulator insert 88 surrounding the fluid passageway 90 forms a valve seat 92 against which a valve element in the form of a ruby ball 94 seats, to control the flow of fluid through the fluid passageway 90. Of course, to accomplish this the diameter of the ruby ball 94 must be larger than the diameter of the valve seat 92.

A pressure spring 96 is disposed immediately below and in contact with the ruby ball 94, to bias the ruby ball against the valve seat 92 to keep the fluid passageway 90 closed until a fluid pressure differential between the inlet and the outlet exceeds a selected valve opening pressure. The pressure spring 96 is supported at an end opposite the ruby ball 94 by a first surface 98 of a rotor assembly 100 which will be described in greater detail below.

The fluid flow control device 20 of the present invention advantageously provides means for adjusting the amount of bias applied to the ruby ball 94 by the pressure spring 96 in order to vary the selected valve opening pressure. Such adjusting means includes a fixed dual concentric stair-step array 102 (see FIGS. 7 and 8) and an overlying rotor assembly 100 (see FIGS. 9–11). A second surface 104 of the rotor assembly 100 is supported by the dual concentric stair-step array 102, and the rotor assembly is rotatable in response to an applied magnetic field to permit magnetic induction adjustments of the valve mechanism.

The dual concentric stair-step array 102 includes a central rotor pivot 106, a plurality of inner steps 108 which surround the rotor pivot, and a corresponding plurality of outer steps 110 which extend peripherally about the inner steps. The inner and outer steps 108 and 110 are constructed so that those steps opposite to one another with respect to the central rotor pivot 106 subtend the same arch and are located at the same level. The stair-step array 102 further includes an outer ring 112 which serves to capture a portion of the rotor assembly 100 therein, a supporting bracket 114 and a lock lever pivot holder 116 which are utilized in connection with a pin actuating mechanism 118 to be described in greater detail below.

The rotor assembly 100, shown best in FIGS. 9–14, includes a magnet 120 embedded within a base 122. A rotor cap 124 is fixed to an upper surface of the base 122 over the magnet 120 to seal the magnet therebetween and to also provide the first surface 98 on which the pressure spring 96 rests. The rotor cap 124 includes a central aperture 126 surrounded by a cylindrical pressure spring-guide flange 128, and a peripheral compression spring-retaining flange 130 which is utilized to help retain a compression spring 132 in a proper position upon the first surface 98. The lower surface of the base 122 defines the second surface 104 of the rotor assembly 100. This portion of the base 122 includes an inner leg 134 which is adapted to bear against a selected one of the plurality of inner steps 108, and an outer leg 136 which is disposed diametrically opposite the inner leg and is adapted to bear against a selected one of the plurality of outer steps 110. The inner and outer legs 134 and 136 extend the same distance downwardly from the base 122. Further, a base central aperture 138 extends centrally through the base 122 and in alignment with the central aperture 126 of the rotor cap, which apertures are configured to permit passage of the central rotor pivot 106 therethrough.

When the rotor assembly 100 is assembled to the stair-step array 102 such that the inner and outer legs 134 and 136 bearing against the diametrically opposite and corresponding inner and outer steps 108 and 110 of the stair-step array, the first surface 98 of the rotor assembly 100, provided by the rotor cap 124, provides a lower seating surface for both the small pressure spring 96 and the much larger compression spring 132. As noted previously, the pressure spring urges the ruby ball 94 into engagement with the valve seat 92 to control the flow of fluid through the fluid passageway 90 of the flow regulator insert 88. The compression spring 132 bears against the rotor cap 124 at one end, and against a portion of the valve housing 36 surrounding the threaded aperture 86 so as to constantly urge the rotor assembly 100 into contact with the stair-step array 102.

The pressure applied by the pressure spring 96 to the ruby ball 92 may be adjusted by rotating the rotor assembly 100 relative to the stair-step array 102. It will be understood that by simply rotating the rotor assembly 100, the vertical height of the rotor assembly relative to the stair-step array 102 may be varied. Positioning the inner and outer legs 134 and 136 on higher inner and outer steps 108 and 110 tends to compress the pressure spring 96, thereby increasing the valve opening pressure in contrast with the positioning of the legs on lower steps.

Figure 1:
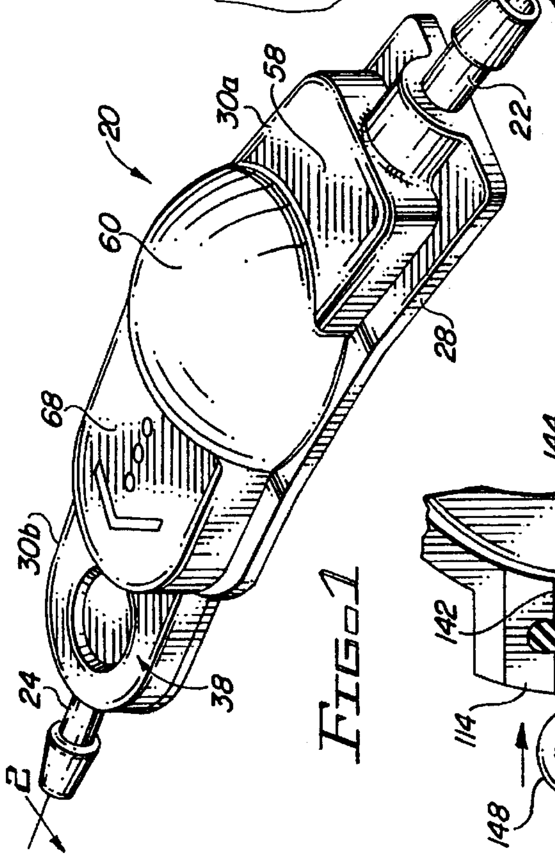
FIG. 1 is a perspective view of an adjustable flow control valve embodying the invention.
Figure 4:
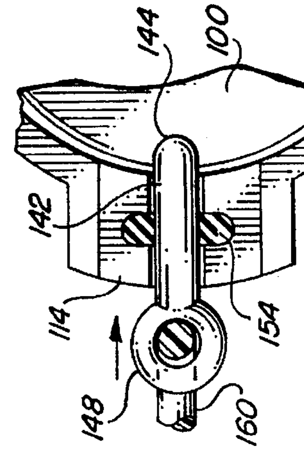
FIG. 4 is an enlarged, fragmented and partially sectional view taken generally along the line 4—4 of FIG. 2

In order to adjust the rotational position of the rotor assembly 100 relative to the stair-step array 102 when the fluid flow control device 20 is subcutaneously implanted, an external magnetic tool 140 having diametrically opposite north and south magnetic poles (see FIG. 1). When the magnetic tool 140 is placed over the valve housing 136 such that magnetic flux coupling occurs between the magnet 120 and the magnetic tool, the rotor assembly 100 will be lifted vertically upwardly away from the stair-step array 102 against the force of the compression spring 132, thereby disengaging the inner and outer legs 134 and 136 from the inner and outer steps 108 and 110. The rotor assembly 100 may then be freely rotated about the central rotor pivot 106 to place the inner and outer legs 134 and 136 on a desired corresponding pair of inner and outer steps 108 and 110 of the stair-step array 102 to provide the fluid flow control device 20, and specifically the valve mechanism, with a desired valve opening pressure. When the magnetic tool 40 is removed from proximity with the magnet 120, the magnetic flux coupling between the two is broken, thereby allowing the compression spring 132 to again force the rotor assembly 100 downwardly into contact with the stair-step array 102.

It is sometimes desirable to provide a positive locking mechanism which will make it impossible to rotate the rotor assembly 100 relative to the stair-step array 102 even in the presence of magnetic field or flux coupling between the magnet 120 and the magnetic tool 140, unless an additional "unlocking" step is performed. To accomplish this, the pin activating mechanism 118 briefly mentioned above is provided. More specifically, a pin 142 is provided which has a first blunt end designed to engage vertical slots or detents 146 provided in the base 122 of the rotor assembly 100, and a second end 148 which is configured to provide an eyelet. The valve housing 36 and the supporting bracket 114 of the stair-step array 102 cooperate to provide a slot 150 through which the pin 142 may reciprocate, and an internal cavity 152 into which an O-ring 154 is positioned. The O-ring 154 engages the pin 142 and adjacent portions of the valve housing 136 and the supporting bracket 114 to prevent fluid leakage from the flushing reservoir 40 into the valve housing 36. The detents 146 provided in the outer periphery of the base 122 are arranged such that when any one of such detents is aligned with the first end 144 of the pin 142, the inner and outer legs 134 and 136 of the rotor assembly 100 are properly positioned over a corresponding set of inner and outer steps 108 and 110 of the stair-step array. When the pin 142 extends sufficiently through the slot 150 so that the first end thereof 144 extends into one of the detents 146, the rotor assembly 100 cannot rotate relative to the stair-step array 102.

To control the position of the pin 142, a lever assembly 156 is provided which includes a cylindrical pivot 158, an eyelet-engaging shaft 160 which extends from the pivot 158 to engage the second end 148 of the pin 142, a lock-paddle lever 162 which extends from the pivot 158 into the flushing reservoir 40, and a biasing lever 164 which extends from a portion of the lock-paddle lever angularly downwardly to engage the bottom plate 46 underlying the flushing reservoir. The biasing lever 164 effectively causes the lever assembly to be normally pivoted such that the pin 142 is urged through the slot 150 into engagement with a selected one of the detents 146. However, the pin 142 can be withdrawn through the slot 150 by pressing downwardly on the dome 60 overlying the flushing reservoir 40 so as to also press downwardly on the lock-paddle lever 162, thus overcoming the force of the biasing lever 164. When the lock-paddle lever 162 is pressed downwardly, the lever assembly 156 pivots so that the shaft 160 pulls on the second end 148 of the pin 142 to withdraw the pin partially through the slot 150 a sufficient distance to disengage the first end 144 of the pin from an adjacent detent 146. Of course, when the downward pressure on the lock-paddle lever 162 is removed, the biasing lever 164 automatically pivots the lever assembly 156 to once again cause the first end 144 of the pin 142 to seek to engage a selected detent 146.

Accordingly, once the fluid flow control device 20 has been properly subcutaneously implanted, the valve opening pressure of the valve mechanism can be adjusted utilizing a two-step procedure. First, percutaneous pressure must be applied to the dome 60 sufficiently to press the lock-paddle lever 162 downwardly so as to pivot the lever assembly in a manner causing the first end 144 of the pin 142 to disengage an adjacent detent 146 in the periphery of the base 122 of the rotor assembly 100 (see FIGS. 5 and 6). Next, the external magnetic tool 140 is brought into close proximity with the magnet 120 embedded within the base 122 to permit the rotational position of the rotor assembly 100 to be varied, as desired, relative to the stair-step array 102, through magnetic induction coupling between the external magnetic tool 140 and the magnet 120. When the rotor assembly 100 is properly positioned relative to the stair-step array 102, the percutaneous pressure applied to the dome 60 is removed, thus permitting the biasing lever 164 to urge the lever assembly 156 in a direction causing the first end 144 of the pin 142 to seek to engage an adjacent one of the detents 146 (see FIG. 4). With the pin 142 so positioned, the rotor 100 is incapable of rotating relative to the stair-step array 102, regardless of the presence or absence of the magnetic tool 140 in proximity with the magnet 120. When the magnetic tool 140 is removed from the vicinity of the magnet 120, the compression spring 132 urges the rotor assembly 100 downwardly into positive contact with the stair-step array, thus ensuring proper performance of the fluid flow control device.

FIGS. 15–18 illustrate an alternative embodiment of the fluid flow control device 20', wherein functional equivalent elements of the device 20' similar to those described above in connection with the fluid flow control device 20 having the same reference numbers. In this embodiment of the fluid flow control device 20', the pin actuating mechanism 118 has been removed. This is the only substantive change between the two embodiments. Other small changes include the configuration of the inner and outer legs 134' and 136' which, it will be noted, are in the form of nubs which depend from the base 122' Further, the rotor cap 124' is integrally molded with the base 122, and is provided a lock-step tab 166 which interacts with a portion of the valve housing 36 to function as a stop to limit rotation of the rotor assembly 100 relative to the stair-step array to less than 360°. Further, it will be noted that a shape of the flow regulator insert 88' is slightly different from the flow regulator insert 88 illustrated in FIG. 14. Otherwise, the fluid flow control device 20' functions the same as the fluid flow control device 20 of FIGS. 1–14. Again, the primary difference lying in the fact that there is no pin actuating mechanism 118 that must be disengaged in order to rotate the rotor assembly 100 relative to the stair-step array 102 through magnetic induction coupling between the external magnetic tool 140 and the magnet 120.

From the foregoing it is to be appreciated that the present invention provides a flow control device 20 or 20' for use in a subcutaneously implanted physiological shunt system, wherein the valve opening pressure may be selectively adjusted when subcutaneously implanted. The construction of the flow control devices 20 and 20' of the present invention permits selective distal and proximal flushing of the devices through the application of manual percutaneous pressure. The present invention provides devices by which the flow of cerebrospinal fluid out of a brain ventricle can be controlled while preventing the backflow of fluid into the brain ventricle, and inhibiting excessive drainage through the physiological shunt in the presence of excessive downstream suction.

Although two particular embodiments of the invention have been described in detail for purposes of illustration, various modifications may be made without departing from the spirit and scope of the invention. Accordingly, the invention is to be limited, except as by the appended claims.

We claim:

1. A subcutaneously implantable and percutaneously adjustable fluid flow control device, comprising:

an inlet for the control device;

an outlet for the control device spaced from the inlet; and a valve apparatus for controlling fluid flow from the inlet to the outlet, the valve apparatus comprising:

a valve housing including a fluid passageway therethrough having a peripheral surface forming a valve seat;

a valve element adjacent to the valve seat;

means for biasing the valve element against the valve seat to keep the fluid passageway closed until a fluid pressure differential between the inlet and the outlet exceeds a selected valve opening pressure; and means for adjusting a bias applied to the valve element by the biasing means, the adjusting means including a fixed dual concentric stair-step array and an overlying rotor assembly having a first surface which supports the biasing means and a second surface which is supported by the dual concentric stair-step array, wherein the rotor assembly is rotatable in response to a percutaneously-applied magnetic field and such rotation of the rotor assembly permits selected seating of the second surface on the stair-step array to raise or lower the rotor assembly with respect to the stair-step array.

2. The fluid flow control device of claim 1, wherein the dual concentric stair-step array includes a central rotor pivot, a plurality of inner steps surrounding the rotor pivot, and a plurality of outer steps extending peripherally about the inner steps, and wherein the rotor assembly includes a magnet imbedded within a base having an inner leg adapted to bear against a selected one of the plurality of inner steps, an outer leg disposed diametrically opposite the inner leg and adapted to bear against a selected one of the plurality of outer steps, and a central aperture through which the rotor pivot extends.

3. The fluid flow control device of claim 2, wherein the rotor assembly further includes a rotor cap fixed to the base on a side thereof opposite the inner and outer legs, the rotor cap providing the first surface of the rotor assembly and including a central aperture aligned with the central aperture of the base, through which the rotor pivot extends.

4. The fluid flow control device of claim 1, wherein the valve apparatus further includes a spring having one end bearing against a portion of the valve housing adjacent to the fluid passageway, and another end bearing against the first surface of the rotor assembly.

5. The fluid flow control device of claim 1, wherein the valve housing includes a flow regulator insert which defines the fluid passageway, threaded into an aperture of the valve housing.

6. The fluid flow control device of claim 1, including means for locking the rotor assembly into one of several possible rotational positions relative to the stair-step array, and means for disengaging the locking means to permit rotation of the rotor assembly in response to the magnetic field.

7. The fluid flow control device of claim 6, wherein the locking means comprises a pin having a first end that engages one of a plurality of detents in an outer peripheral surface of the rotor assembly, and wherein the disengaging means comprises pin actuating means for moving the pin between a first position wherein the first end of the pin engages one of the plurality of detents, and a second retracted position.

8. The fluid flow control device of claim 7, wherein the pin actuating means comprises a pivotable lever including a shaft that engages a second end of the pin, and a manually actuated lever which is biased to urge the pin into its first position.

9. The fluid flow control device of claim 1, including a pump situated between the inlet and the valve means, wherein the pump provides means for flushing fluid through the fluid flow control device by the percutaneous application of pressure to the pump.

10. The fluid flow control device of claim 9, including means for occluding a portion of a fluid flow path through the fluid flow control device adjacent to the inlet by the percutaneous application of pressure to the device, and means for occluding a portion of the fluid flow path adjacent to the outlet by the percutaneous application of pressure to the device.

11. The fluid flow control device of claim 1, including siphon control device means situated between the valve means and the outlet, for preventing fluid flow through the device in the absence of negative hydrostatic pressure at the outlet.

12. A subcutaneously implantable and percutaneously adjustable fluid flow control device, comprising:

an inlet for the control device;

an outlet for the control device spaced from the inlet;

a valve apparatus for controlling fluid flow from the inlet to the outlet, the valve apparatus comprising:

a valve housing including a fluid passageway therethrough having a peripheral surface forming a valve seat;

a valve element adjacent to the valve seat; and means for biasing the valve element against the valve seat to keep the fluid passageway closed until a fluid pressure differential between the inlet and the outlet exceeds a selected valve opening pressure, the biasing means including a fixed stair-step array and an adjacent rotor assembly adapted to rotate relative to the stair-step array in response to a percutaneously-applied magnetic field, wherein such rotation raises or lowers the rotor assembly with respect to the stair-step array; and a pump situated between the inlet and the valve means, wherein the pump provides means for flushing fluid through the device by the percutaneous application of pressure to the pump.

13. The fluid flow control device of claim 12, including siphon control device means situated between the valve means and the outlet, for preventing fluid flow through the device in the absence of negative hydrostatic pressure at the outlet.

14. The fluid flow control device of claim 12, wherein the stair-step array includes a central rotor pivot, a plurality of inner steps surrounding the rotor pivot, and a plurality of outer steps extending peripherally about the inner steps, and wherein the rotor assembly includes a magnet imbedded within a base having an inner leg adapted to bear against a selected one of the plurality of inner steps, an outer leg disposed diametrically opposite the inner leg and adapted to bear against a selected one of the plurality of outer steps, and a central aperture through which the rotor pivot extends.

15. The fluid flow control device of claim 14, wherein the biasing means includes a spring disposed between the valve element and the rotor assembly.

16. The fluid flow control device of claim 15, wherein the rotor assembly includes a rotor cap fixed to the base on a side thereof opposite the inner and outer legs, and a central aperture aligned with the central aperture of the base, through which the rotor pivot extends.

17. The fluid flow control device of claim 14, wherein the valve apparatus further includes a spring having one end bearing against a portion of the valve housing surrounding the fluid passageway, and another end bearing against the rotor assembly.

18. The fluid flow control device of claim 17, including a flow regulator insert threaded into an aperture of the valve housing to define the fluid passageway.

19. The fluid flow control device of claim 12, including means for locking the rotor assembly into one of several possible rotational positions relative to the stair-step array, and means for disengaging the locking means to permit rotation of the rotor assembly in response to the magnetic field, wherein the locking means comprises a pin having a first end that engages one of a plurality of detents in an outer peripheral surface of the rotor assembly, and wherein the disengaging means comprises pin actuating means for moving the pin between a first position wherein the first end of the pin engages one of the plurality of detents, and a second retracted position.

20. The fluid flow control device of claim 19, wherein the pin actuating means comprises pivotable lever including a shaft that engages a second end of the pin, and a manually actuated lever disposed within the pump and biased so as to urge the pin into its first position.

21. A subcutaneously implantable and percutaneously adjustable fluid flow control device, comprising:

an inlet for the control device;

an outlet for the control device spaced from the inlet;

valve means for controlling fluid flow from the inlet to the outlet, the valve means comprising:

a valve housing having a threaded aperture and a flow regulator insert threaded into the threaded aperture to define a fluid passageway therethrough, the fluid passageway having a peripheral surface forming a valve seat;

a valve element adjacent to the valve seat;

first spring means for biasing the valve element against the valve seat to keep the fluid passageway closed until a fluid pressure differential between the inlet and the outlet exceeds a selected valve opening pressure;

means for adjusting a bias applied to the valve element by the first spring means, the adjusting means including a fixed dual concentric stair-step array and an overlying rotor assembly having a first surface which supports an end of the first spring means, and a second surface which is supported by the dual concentric stair-step array, wherein the rotor assembly is rotatable in response to a magnetic field and such rotation of the rotor assembly permits selected seating of the second surface on the stair-step array to raise or lower the rotor assembly with respect to the stair-step array, the dual concentric stair-step array including a central rotor pivot, a plurality of inner steps surrounding the rotor pivot, and a plurality of outer steps extending peripherally about the inner steps, the rotor assembly including a magnet embedded within a base having an inner leg adapted to bear against a selected one of the plurality of inner steps, an outer leg disposed diametrically opposite the inner leg and adapted to bear against a selected one of the plurality of outer steps, a central aperture through which the rotor pivot extends, and a rotor cap fixed to the base on a side thereof opposite the inner and outer legs, the rotor cap providing the first surface of the rotor assembly and including a central aperture aligned with the central aperture of the base through which the rotor pivot extends; and second spring means having one end bearing against a portion of the valve housing and another end bearing against the first surface of the rotor assembly; and a pump situated between the inlet and the valve means, wherein the pump provides means for flushing fluid through the device by the percutaneous application of pressure to the pump.

22. The fluid flow control device of claim 21, including siphon control device means situated between the valve means and the outlet, for preventing fluid flow through the device in the absence of negative hydrostatic pressure at the outlet.

23. The fluid flow control device of claim 21, including means for locking the rotor assembly into one of several possible rotational positions relative to the stair-step array, and means for disengaging the locking means to permit rotation of the rotor assembly in response to the magnetic field, wherein the locking means comprises a pin having a first end that engages one of a plurality of detents in an outer peripheral surface of the rotor assembly, and wherein the disengaging means comprises pin actuating means for moving the pin between a first position wherein the first end of the pin engages one of the plurality of detents, and a second retracted position.

24. The fluid flow control device of claim 23, wherein the pin actuating means comprises pivotable lever including a shaft that engages a second end of the pin, and a manually actuated lever disposed within the pump and biased so as to urge the pin into its first position.

25. A subcutaneously implantable and percutaneously adjustable fluid flow control device, comprising:

an inlet for the control device;

an outlet for the control device spaced from the inlet; and a valve apparatus for controlling fluid flow from the inlet to the outlet, the valve apparatus comprising:

a valve housing including a fluid passageway therethrough having a peripheral surface forming a valve seat;

a valve element adjacent to the valve seat; and an assembly for biasing the valve element against the valve seat to keep the fluid passageway closed until a fluid pressure differential between the inlet and the outlet exceeds a selected valve opening pressure, the biasing assembly including a fixed stair-step array and an adjacent rotor assembly adapted to rotate relative to the stair-step array in response to a percutaneously-applied magnetic field, wherein such rotation raises or lowers the rotor assembly with respect to the stair-step array.

26. The fluid flow control device of claim 25, wherein the stair-step array includes a central rotor pivot, a plurality of inner steps surrounding the rotor pivot, and a plurality of outer steps extending peripherally about the inner steps, and wherein the rotor assembly includes a magnet imbedded within a base having an inner leg adapted to bear against a selected one of the plurality of inner steps, an outer leg disposed diametrically opposite the inner leg and adapted to bear against a selected one of the plurality of outer steps, and a central aperture through which the rotor pivot extends.

27. The fluid flow control device of claim 26, wherein the rotor assembly further includes a rotor cap fixed to the base on a side thereof opposite the inner and outer legs, the rotor cap providing the first surface of the rotor assembly and including a central aperture aligned with the central aperture of the base, through which the rotor pivot extends.

28. The fluid flow control device of claim 25, wherein the valve apparatus further includes a spring having one end bearing against a portion of the valve housing adjacent to the fluid passageway, and another end bearing against the first surface of the rotor assembly.

29. The fluid flow control device of claim 25, including a device for locking the rotor assembly into one of several possible rotational positions relative to the stair-step array, and a device for disengaging the locking device to permit rotation of the rotor assembly in response to the magnetic field, wherein the locking device comprises a pin having a first end that engages one of a plurality of detents in an outer peripheral surface of the rotor assembly, and wherein the disengaging device comprises pin actuating means for moving the pin between a first position wherein the first end of the pin engages one of the plurality of detents, and a second retracted position.

30. The fluid flow control device of claim 29, including a pump situated between the inlet and the valve apparatus, wherein the pump provides means for flushing fluid through the device by the percutaneous application of pressure to the pump, and wherein the pin actuating means comprises pivotable lever including a shaft that engages a second end of the pin, and a manually actuated lever disposed within the pump and biased so as to urge the pin into its first position.

* * * * *

UNITED STATES PATENT AND TRADEMARK OFFICE

CERTIFICATE OF CORRECTION

PATENT NO. : 5,637,083

DATED : June 10, 1997

INVENTOR(S) : Bertrand et al.

Figure 18:
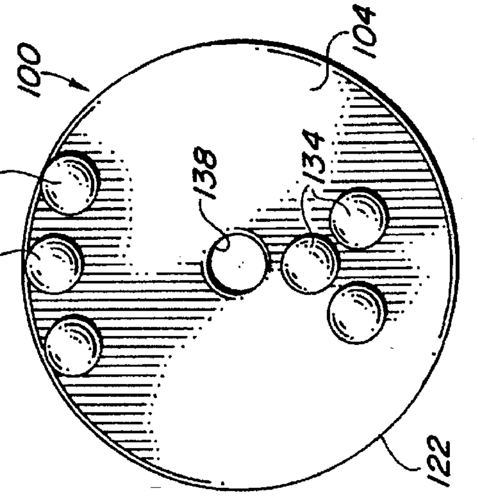
FIG. 18 bottom plan view of the rotor assembly base of FIG. 17.
Figure 17:
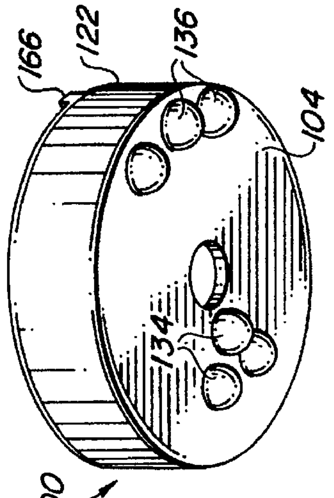
FIG. 17 is a bottom and side perspective view of the rotor assembly base partially shown in FIGS. 15 and 16.
Figure 15:
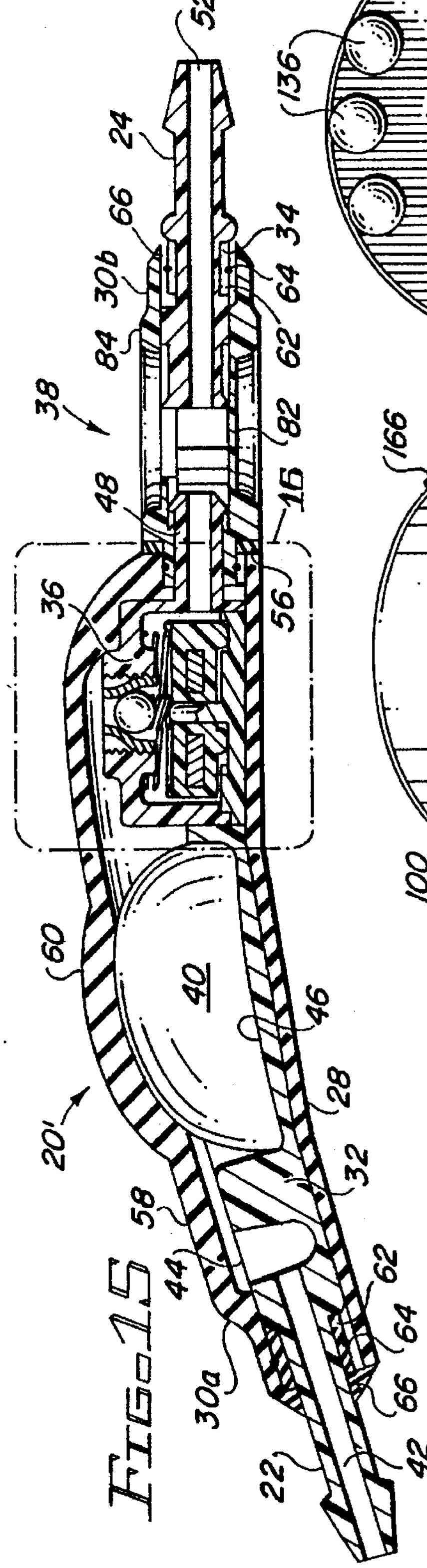
FIG. 15 is a vertical section similar to that shown in FIG. 2, illustrating another embodiment of the invention.
Figure 16:
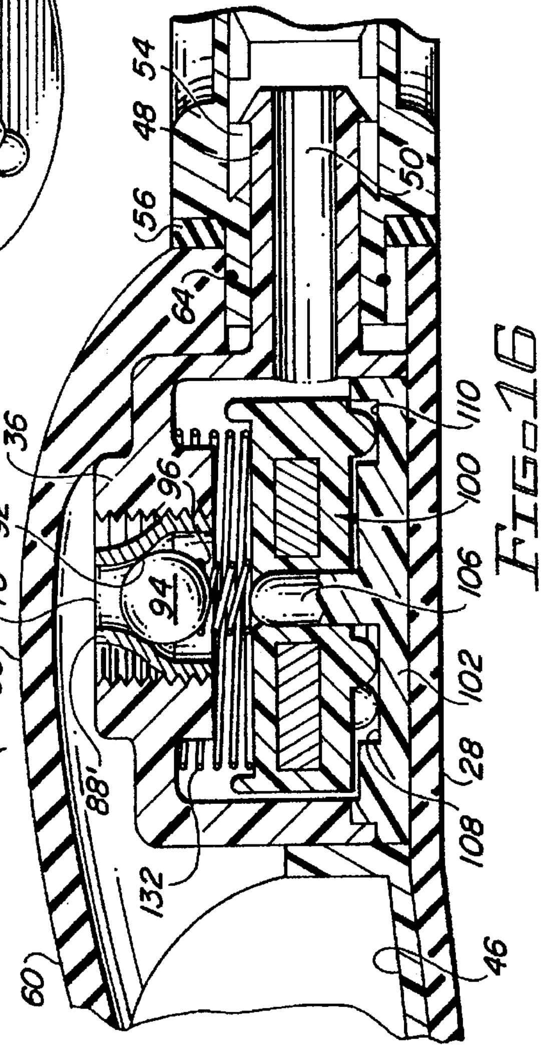
FIG. 16 is an enlarged, fragmented section taken generally of the area indicated by the line 16 in FIG. 15.

It is certified that error appears in the above-identified patent and that said Letters Patent is hereby corrected as shown below:

| | | | |
|---|---|---|---|
| **Col. 1, Line 62:** | **"provide."** | **should be** | **"provide"** |
| **Col. 4, Line 15:** | **"FIG. 2"** | **should be** | **"FIG. 2;"** |
| **Col. 4, Line 43:** | **"us"** | **should be** | **"is"** |
| **Col. 4, Line 61:** | **"FIG. 18 bottom"** | **should be** | **"FIG. 18 is a bottom"** |
| **Col. 7, Line 43:** | **"though"** | **should be** | **"through"** |
| **Col. 11, Line 7:** | **"122' Further"** | **should be** | **"122'. Further"** |

Signed and Sealed this

Sixth Day of October, 1998

*Attest:*

Bruce Lehman

BRUCE LEHMAN

*Attesting Officer*

*Commissioner of Patents and Trademarks*